United States Patent [19]

Lersmacher et al.

[11] 4,338,358
[45] Jul. 6, 1982

[54] METHOD OF PRODUCING CUVETTES FOR THE FLAMELESS ATOMIC ABSORPTION SPECTROSCOPY

[75] Inventors: Bernhard Lersmacher, Aachen, Fed. Rep. of Germany; Ludovicus W. J. van Kollenburg, Eindhoven, Netherlands; Leonardus C. Bastings, deceased, late of Valkenswaard, Netherlands; Friedrich J. de Haan, administrator, Dommelen, Netherlands

[73] Assignee: U.S. Philips Corporation, New York, N.Y.

[21] Appl. No.: 45,909

[22] Filed: Jun. 6, 1979

[30] Foreign Application Priority Data

Jun. 12, 1978 [DE] Fed. Rep. of Germany ....... 2825759

[51] Int. Cl.³ .............................................. B05D 3/02
[52] U.S. Cl. .................................. 427/227; 427/228; 427/242; 427/429; 427/292; 427/299
[58] Field of Search ............... 427/228, 227, 249, 242, 427/299, 246, 292

[56] References Cited

U.S. PATENT DOCUMENTS

| 3,238,054 | 3/1966 | Bickerdike et al. | 427/227 |
| 3,321,327 | 5/1967 | Blanchard et al. | 427/249 |
| 3,677,795 | 7/1972 | Boskros et al. | 427/249 |
| 3,682,682 | 8/1972 | Nakamura et al. | 427/228 |
| 3,725,110 | 4/1973 | Rodgers et al. | 427/249 |
| 3,854,979 | 12/1974 | Rossi | 427/228 |
| 3,949,106 | 4/1976 | Araki et al. | 427/249 |
| 3,969,124 | 7/1976 | Stewart | 427/249 |
| 4,100,322 | 7/1978 | Seibold et al. | 427/228 |

FOREIGN PATENT DOCUMENTS 49-1395   1/1974   Japan ................... 427/242

Primary Examiner—Norman Morgenstern
Assistant Examiner—Janyce A. Bell
Attorney, Agent, or Firm—Paul R. Miller

[57] ABSTRACT

The life of AAS cuvettes coated with pyrolytic graphite is increased to more than 3000 injections when the coated substrata are additionally coated at least once with pyrolytic graphite, pyrolytic graphite layers having an overall thickness of 20–80 $\mu$m then being applied.

8 Claims, No Drawings

METHOD OF PRODUCING CUVETTES FOR THE FLAMELESS ATOMIC ABSORPTION SPECTROSCOPY

The invention relates to a method of producing cuvettes for the flameless atomic absorption spectroscopy (AAS) wherein carbon substrata are coated with pyrolytic graphite.

Such cuvettes are used as receptacles and heating devices for the sample to be analysed. Tubular bodies are particularly used as cuvettes (German Offenlegungsschrift No. 2,006,032, German Offenlegungsschrift 2,148,777). Generally, the cuvettes consist of electrically conducting material having a high temperature resistance, since heating of the sample to be analysed is usually effected by resistance heating of the cuvettes with direct passage of an electric current. Heating can, of course, alternatively be effected in a different manner, for example by induction or by radiation.

The material which is preferably used for such cuvettes is carbon, particularly in the form of electro-graphite of a spectrally pure grade. In addition, it is known to produce cuvettes of vitreous carbon (United Kingdom Patent Specification No. 1,323,100).

Owing to the porosity of the above-mentioned graphite, analysis material penetrates into the wall of the cuvettes so that, when the cuvette is frequently used residual material of an analysis has a negative effect on the results of subsequent analyses. This phenomena is known as "memory effect". In addition, the penetration of this analysis material into the walls of the cuvettes has also a negative effect on the detection limit and the sensitivity of the analysis. Especially the useful life of the cuvettes is considerably shortened owing to the penetration of analysis material into the graphite walls, as this material has a very high corrosive effect during the analysis, wherein temperatures up to 3000° C. may occur.

In order to limit or to obviate the abovementioned drawback to the full, it is recommended to seal the pore channels (and the grain boundaries which are very sensitive to corrosion) of the graphite. This is, for example, effected by the provision of a thin layer of pyrolytic graphite, which forms already an effective diffusion barrier in a layer thickness of a few micrometers (5–10 $\mu$m). This is inter alia manifest from the fact that, for example, both the sensitivity (sensitivity, mean-absorbance) and especially the life is considerably increased, as appeared from measurements. Summarizing, the state of the art is such that uncoated cuvettes of graphite can withstand 10–100 analyses (United Kingdom Patent No. 1,323,100, mentions 200 analyses); for cuvettes coated with pyrolytic graphite the possibility of re-use is increased, the sensitivity being improved at the same time, but the statements in the literature about the extent to which the life is increased are partly contradicting and without engagement. In this respect, reference is made to the publication by Manning and Edinger in "Atomic absorption News Letter" vol. 15, no. 2, March–April 1976, pages 42–44, where a so-called "in situ" coating is described. From the specifications given there it can be derived that an increased sensitivity is indeed obtained, but that the possibility to re-use the cuvettes for approximately a hundred times does not furnish particular advantages with respect to the uncoated cuvettes. In addition, the method of "in situ" coating is very complicated, the quality of the coating is difficult to check and the coating operation must apparently be repeated after relatively short periods of time, for example after not more than 8 analyses.

It is an object of the invention to provide a cuvette having a high sensitivity, but whose primary improvement consists, however, in a considerably increased life. The technical significance of long lives becomes particularly clear when the object of automised AAS apparatus, as they are, for example, used for the routine monitoring of, for example, water and/or air pollution, is considered.

According to the invention, a method of the type mentioned in the opening paragraph is characterized in that the coated substrata are coated at least once with pyrolytic graphite and in that pyrolytic graphite layers having a total thickness of 20–80 $\mu$m are applied.

Layers, having a total thickness of 20–40 $\mu$m are preferably applied.

It is not recommended to produce layers thicker than 80 $\mu$m, because with layers of such a thickness there is a risk of flaking. In addition, the electric resistance of a cuvette varies considerably versus an increasing layer thickness, which often appears to have a negative effect on the operation of the analysis apparatus used.

It is recommended to effect at least one of the consecutive coating operations by means of hot-wall pyrolysis. The hot-wall pyrolysis is known from "Philips Technisch Tijdschrift" vol. 37 (1977) no. 7, pages 161–168. The use of this method has the advantage that a large number (of the mass-produced) cuvettes can be coated simultaneously, which is important for reasons of economy. The method is independent of the shape and the position of the individual cuvettes, because the heating to uniform temperatures and therefore the uniformity of the deposited layers in the interior of the cuvettes is ensured. The individual cuvettes need not be accommodated individually oriented in the reactor vessel, but are simply dumped into the vessel. This may be considered as a certain drawback of the method, because it cannot be prevented that regions of contact between the cuvettes are created in the coating space, which results in a non-uniform thickness of the outer coating. This drawback of the method is compensated to a very great extent by the fact that the heap of cuvettes is shaken, which means that during subsequent coating operations each individual cuvette occupies a different position in the reactor and also has other points of contact with the adjacent cuvettes as a result of this redistribution. This shaking or redistribution after each preceding coating operation can be effected several times, but it appeared that it is sufficient to shake only once, that is to say to apply the layers in two steps.

The substrata to be coated generally consist of graphite, particularly of electro-graphite. In some cases it is efficient to coat substrata of vitreous carbon. It is particularly advantageous to coat by the method according to the invention also substrata of carbonised synthetic resin bonded fabric on the basis of hardenable synthetic resins (for example phenolic resin or cresol resin) which are capable of being converted into vitreous carbon, and cotton fabric. German Patent Application P. 2,702,189,2 proposed such substrata for cuvettes.

In a further embodiment of the method according to the invention the surface areas of the substrate, particularly the "inside surface" of the cuvettes which, at the start of the analysis comes into direct contact with the sample to be analysed, are made as smooth as possible (polished) prior to coating.

By means of the method according to the invention cuvettes are produced which are remarkable for a high degree of uniformity and a proper structure of the protective layers of pyrolytic graphite in the interior but also at the exterior. It was surprisingly found, during numerous measurements, that the cuvettes produced with the method according to the invention and an extremely long life (an extremely high number of injections, analyses) when the pyrolytic graphite layer had a thickness of over 20 μm, a thickness of approximately 30–40 μm in particular.

EXAMPLE I 600 tubular graphite cuvettes, having a length of 28 mm, an outside diameter of 8 mm and an inside diameter of 6 mm, were simultaneously introduced in a hot-wall reaction vessel and provided with a layer of properly oriented pyrolytic graphite in six coating operations, each lasting for 1 hour, so with 5 redistributions. At the end of these operations the overall layer thickness was approximately 37 μm. In a test under real circumstances, wherein each time an analysis solution of aluminium in 0.1 N nitric acid was injected and thereafter the described temperature-time cycle (to T=3000 K.) was passed through, it appears that a cuvette could resist 610 to 1200 of such cycles.

EXAMPLE II

Cuvettes which were produced in the same manner were able to withstand 320 to 700 injections in the same temperature-time cycle when a solution of aluminium in 0.1 N perchlorid acid was injected instead of 0.1 N $HNO_3$.

EXAMPLE III 250 graphite cuvettes were coated in otherwise similar circumstances with properly oriented pyrolytic graphite. However, coating to layer thicknesses of approximately 40 μm was effected in two steps, so the cuvettes were shaken only once.

In the analysing condition described in Examples I and II, lives of >3000 injections were obtained. The tests were stopped after this number of injections, although the cuvettes were still fit for use.

What is claimed is:

1. A method of producing cuvettes for flameless atomic absorption spectroscopy comprising the steps of placing a plurality of carbon substrate in a loose heap in a pyrolysis apparatus, effecting a plurality of separate coatings of pyrolytic graphite on said substrata until an overall thickness of 20–80 μm is applied, and redistributing said plurality of carbon substrata in said apparatus between each coating of pyrolytic graphite.

2. A method as claimed in claim 1, wherein said coatings have an overall thickness of 30–40 μm.

3. A method as claimed in claims 1 or 2, wherein at least one of said plurality of separate coatings is effected by hot-wall pyrolysis.

4. A method as claimed in claims 1 or 2, wherein said carbon substrata are graphite.

5. A method as claimed in claims 1 or 2, wherein said carbon substrata are vitreous carbon.

6. A method as claimed in claims 1 or 2, wherein said carbon substrata are carbonized synthetic resin bonded fabric including thermosetting synthetic resins and cotton fabric, said thermosetting synthetic resins being converted into vitreous carbon.

7. A method as claimed in claims 1 or 2, wherein surface areas of said carbon substrata are polished before said steps of coating.

8. A method as claimed in claim 7, wherein said carbon substrata have interior surfaces which are polished before said steps of coating.

* * * * *